United States Patent [19]

Lue-Hing et al.

[11] Patent Number: 4,804,631
[45] Date of Patent: Feb. 14, 1989

[54] METHOD AND APPARATUS FOR MEASURING CYANIDE

[75] Inventors: Cecil Lue-Hing, Chicago; Nabih P. Kelada, Glen Ellyn, both of Ill.

[73] Assignee: The Metropolitan Sanitary District of Greater Chicago, Chicago, Ill.

[21] Appl. No.: 859,049

[22] Filed: May 2, 1986

[51] Int. Cl.[4] ............................................. G01N 21/75
[52] U.S. Cl. .................................. 436/109; 436/905; 250/304
[58] Field of Search .......................... 436/109, 35, 905; 250/304; 201/1; 203/1, 34, 89

[56] References Cited

U.S. PATENT DOCUMENTS

| | | | |
|---|---|---|---|
| 4,248,598 | 2/1981 | Blunck | 436/905 X |
| 4,265,857 | 5/1981 | Kelada et al. | 422/82 X |
| 4,344,918 | 8/1982 | Takahashi | 422/78 X |
| 4,608,345 | 8/1986 | Goodwin et al. | 436/177 X |
| 4,666,860 | 5/1987 | Blades, et al. | 422/78 X |

FOREIGN PATENT DOCUMENTS 9038684 4/1974 Japan .................................. 436/109

OTHER PUBLICATIONS

Grieve et al., Analytical Chemistry 53(11), pp. 1711-1712.
Botto, et al., Analytical Chemistry 53(14), pp. 2375-2376.

*Primary Examiner*—Benoit Castel
*Assistant Examiner*—Jill Johnston
*Attorney, Agent, or Firm*—Bernard L. Kleinke

[57] ABSTRACT

A system for measuring cyanides in a sample employs a photoillumination component for producing ultraviolet radiation to dissociate cyanides contained in an alkaline sample. The system includes filtering components interposed between the photoillumination components and an alkaline sample to be tested for passing lower frequency ultraviolet radiation to produce an irradiated sample in which cyanides have been dissociated, while blocking high frequency ultraviolet radiation to inhibit thiocyanate dissociation. Thin-film distillation components are included for separating cyanide from the irradiated sample to produce recovered cyanide for measurement purposes, and measuring components are provide for receiving the recovered cyanide generating a recordable signal indicative of recovered cyanide quantity.

11 Claims, 3 Drawing Sheets

METHOD AND APPARATUS FOR MEASURING CYANIDE

TECHNICAL FIELD

This invention relates generally to a method and apparatus for measuring the amount of cyanide in a sample, and it more particularly relates to such a method and apparatus having improved cyanide separation capabilities.

BACKGROUND ART

The toxic compounds called cyanides threaten our health and environment. Harmful to man, and even more so to aquatic life, these compounds are produced and introduced into our environment in many damaging ways, so that it is important to understand and restrict this form of environmental pollution. Measuring the cyanides in a selected sample is one important step in the process of improving the environment.

Of the various existing types and kinds of analytical methology and related apparatus employed to measure cyanides, automated systems have achieved notable results. For example, refer to U.S. Pat. No. 4,265,857, and to a publication entitled "Chemistry of Wastewater Technology" published by Ann Arbor Science Publishers, Inc. of Ann Arbor Michigan, Library of Congress Catalog Card No. 76-50991, ISBN 0 250 40185-1, which are incorporated herein by reference.

As described in Chapter 20 of "Chemistry of Wastewater Technology," such an automated system involves the steps of separation, absorption, and measurement, with ultraviolet irradiation being employed to dissociate cyanides in the process of separation, along with thin-film distillation and chemical absorption techniques.

A typical ultraviolet radiation unit includes an ultraviolet lamp, surrounded by a quartz coil, through which is passed an acidic sample to be tested. The quartz coil passes all of the several energy levels, or spectral lines, of ultraviolet radiation produced by the ultraviolet lamp, of wave lengths between approximately 150 millimicrons and 400 millimicrons. This spectrum of ultraviolet radiation causes the break down of all cyanide complexes, including the strong iron and cobalt cyanide complexes. The cobalt complex is dissociated by the ultraviolet radiation both of approximately 255 millimicrons, and of approximately 310 millimicrons. In this manner, the cyanides are dissociated for subsequent measurement.

The thin-film distillation separates the resulting hydrogen cyanide gas, and the HCN gas is then absorbed in a sodium hydroxide solution for subsequent colorimetric measuring. Thus, all of the cyanides can be detected and measured in a large number of different samples in a continuous, automated manner.

The quartz coil in the conventional irradiation unit of the system is permeable to all, or at least substantially all, of the ultraviolet spectrum, thereby enabling the ultraviolet radiation to break down all of the cyanide complexes in the acidic sample. However, thiocyanate (SCN) is also dissociated, and therefore, is detected along with the cyanides, thereby causing somewhat inaccurate higher cyanide measurements. Thus, dissociation of the thiocyanate is unwanted and undesirable for most applications. Consequently, while the present cyanide detection measurement system is satisfactory for most applications, it would be highly desirable to have a cyanide measurement system, which would dissociate all the cyanide complexes, including the strong cobalt complex, without dissociating thiocyanate.

DISCLOSURE OF INVENTION

Therefore, the principal object of the present invention is to provide a new and improved measurement method and apparatus for indicating the amount of cyanide in a sample, without detecting or indicating the presence of thiocyanate, in a convenient and precise manner.

It is a further object of the present invention to provide such a new and improved method and apparatus, which enables dissociation of strong cyanide complexes, including cobalt and iron complexes, without the dissociation of thiocyanate.

Yet another object of the present invention is to provide such an improved method and apparatus, which requires only simple modifications of exisiting systems.

Briefly, the above and further objects of the present invention are realized by providing a new and improved system for measuring cyanides in liquid samples.

The system includes a filtering component interposed between an ultraviolet photoillumination device and a sample to be tested, for passing only lower frequency ultraviolet radiation to irradiate the sample for breaking up cyanide complexes contained therein, while blocking high frequency ultraviolet radiation to inhibit the dissociation of the thiocyanate.

Thin-film distillation components are included for separating cyanide from the irradiated sample to produce recovered cyanide for measurement purposes, and measuring components are provide for receiving the recovered cyanide and for generating a recordable signal indicative of the amount of recovered cyanide without any indication of thiocyanate.

Thus, the method and apparatus of this invention alleviates the above-mentioned drawbacks of existing techniques. The filter blocks ultraviolet radiation in the range of approximately 150 millimicrons and approximately 290 millimicrons, to inhibit thiocyanate dissociation, while passing the remaining longer ultraviolet wavelengths.

The pH of the sample is raised to enable the strong cobalt cyanide complexes to be completely broken up as well. In this regard, in prior known systems, the samples are acidic, and are irradiated with non-filtered quartz irradiation units to provide a complete dissociation of the cyanide complexes, as well as the release of the unwanted thiocyanate. However, it has been discovered that an alkaline sample combined with the filtered irradiation, achieves total break down of cyanide complexes, without dissociating thiocynate. In this manner, more convenient cyanide measurements are provided, with only a simple modification of existing systems.

BRIEF DESCRIPTION OF DRAWINGS

The above and other objects and features of this invention and the manner of attaining them will become apparent, and the invention itself will be best understood, by reference to the following description of an embodiment of the invention taken in conjunction with the accompanying drawings, wherein.

BEST MODE FOR CARRYING OUT THE INVENTION

Figure 1:
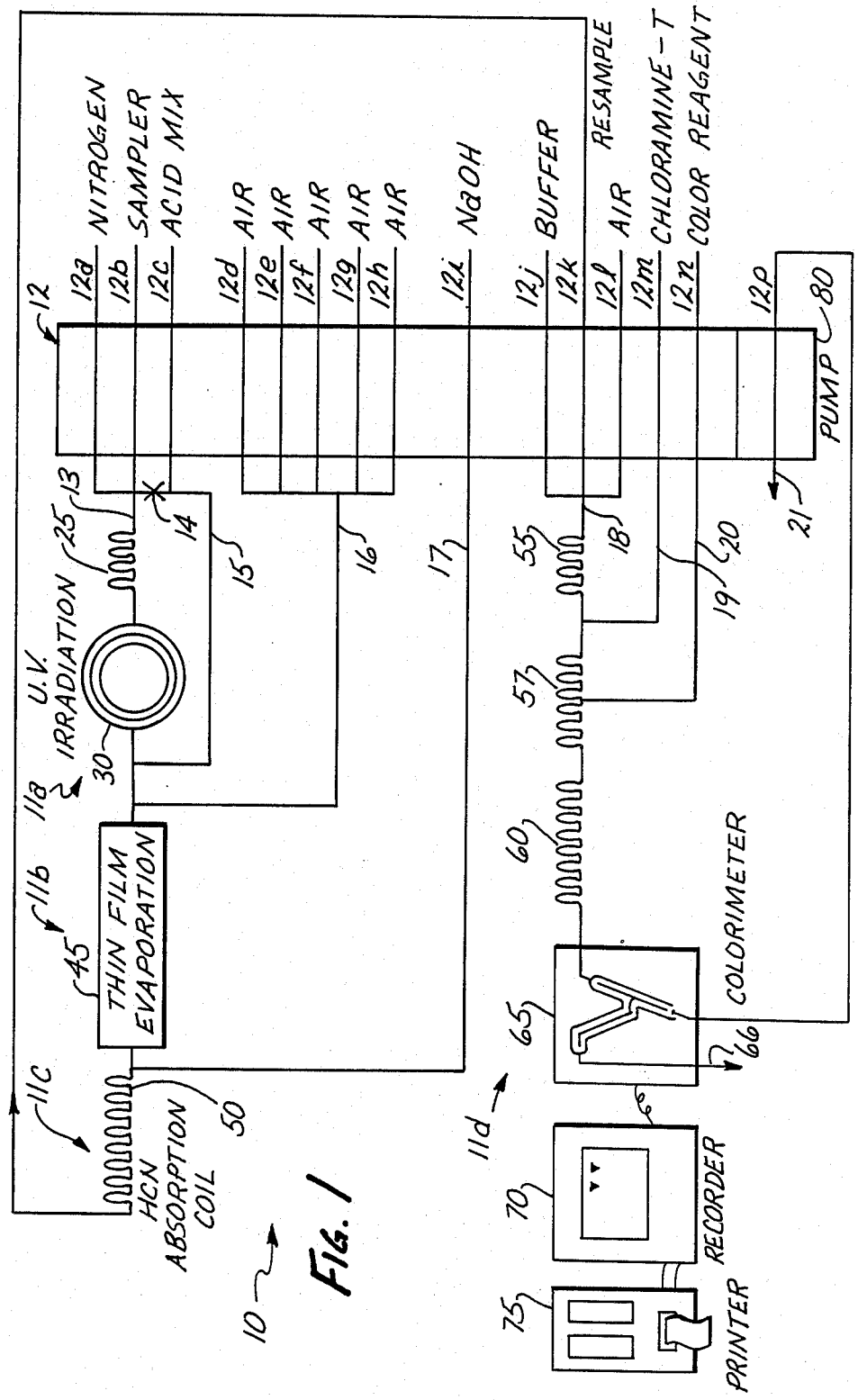
FIG. 1 is a partially schematic, block diagram of a cyanide measuring system constructed according to the present invention.

Referring now to the drawings, and more particularly to FIG. 1, there is shown a cyanide measuring system 10, which is constructed according to the present invention, and which is used to measure the different amounts of different cyanides, contained in a series of different water samples admitted seriatim to the system 10 at an inlet 12B. The system 10 generally comprises a separation section including a photoillumination irradiation unit 11A for causing the break down of cyanide complexes in the water samples being pumped through it. A 11A thin-film distillation unit 11B separates cyanide from the irradiated samples to produce recovered cyanide for measuring purposes. An absorption section 11C provides for the sodium hydroxide absorption of the hydrogen cyanide gas evolved from the samples. A measurement section 11D automatically measures the cyanide in the samples from the section 11C.

A segmented flow pump 12 transfers the samples and reagents to the system 10 at inputs 12A–12N and 12P to outputs, 13, 15–21. The samples (usually made alkaline for preservation) are mixed with a suitable quantity of nitrogen by admitting them to an inlet 13 to a sample mixing coil 25, to provide the vehicle for the segmented flow of the series of water samples to be tested. In the system 10, air can be used in place of nitrogen.

The photoillumination unit 11A is in the form of a filtered ultraviolet irradiation unit 30, which irradiates the series of segmented samples flowing through it from the coil 25, to dissociate the cyanide complexes contained in the samples. The unit 30 emits light in only a limited porton of the ultraviolet spectrum, namely, between approximately 290 millimicrons and approximately 400 millimicrons wavelengths of ultraviolet radiation, for dissociating the cyanides from their cyanide complexes, without dissociating thiocyanate.

The irradiated samples flowing continuously from the outlet of the irradiation unit 30 are mixed with a suitable acid mixture via a line 15, as well as air under pressure received via a line 16. The continuous thin-film evaporation unit 11B receives the aerated acidified samples for separating the cyanides from the samples. The evaporation unit 11B is disclosed more fully in the foregoing mentioned U.S. patent. The thin-film evaporation unit 11B causes hydrogen cyanide gas to be released, together with some water, from the acidified samples in a continuous segmented flow basis. The water is condensed back, and the hydrogen cyanide gas is absorbed via the absorption section 11C.

The segmented samples flowing from the outlet of the thin-film evaporation unit are mixed with sodium hydroxide from a line 17 in the section 11C, which is an absorption coil 50. In this regard, the hydrogen cyanide gas is forced with air through the coil, simultaneously with sodium hydroxide, as more fully described in the foregoing mentioned publication, to recover the hydrogen cyanides in each sample.

The outlet of the absorption coil 50 is pumped back through the pump 12 via a return line 18, to be mixed with a suitable buffer and segmented by air, to a sample mixing coil 55.

The outlet of the sample mixing coil 55 is mixed with chloramine-T from a line 19, in a mixing coil 57, where it is mixed with a color reagent from a line 20 from the pump 12.

The outlet of the mixing coil 57 is connected through a mixing coil 60 to a colorimeter 65 and discharged through a line 66, with the pump 12 driving the system and exhausting it from the line 21.

The colorimeter provides a recordable signal indicative of the recovered cyanide quantities to an input of a recorder 70, connected to a printer 75.

Thus, the method and system of this invention provides dissociation of all cyanide complexes, including cobalt complexes, without thiocyanate interference. It achieves this by employing an alkaline sample with a new and improved ultraviolet irradiation unit, which filters selected ultraviolet energy levels to inhibit the thiocyanate break down.

It is a feature of the present invention to acidify the samples with the acid mixture via line 15, after the irradiation, rather than prior to it, for the purpose of causing the stronger cyanide complexes, such as the cobalt complexes, to break down, without the break down of thiocyanate.

Figure 2:
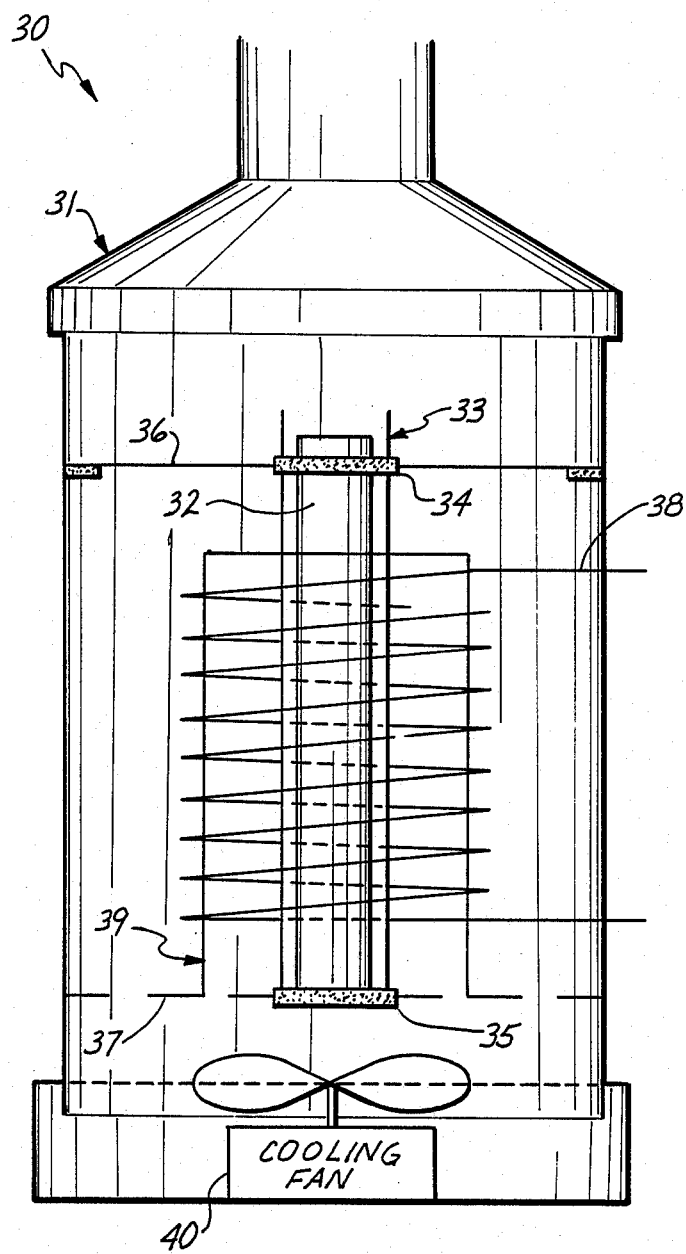
FIG. 2 is schematic diagram of an ultraviolet irradiation unit of the system of FIG. 1.

Considering now the filtered ultraviolet irradiation unit 30 with reference to FIG. 2 unit 30. An opague metal housing 31 confines therein a vertically disposed ultraviolet lamp 32 for emitting a full spectrum of ultraviolet radiation. A clear glass tube 33 surrounds the lamp 32 and is supported vertically by first and second rings 34 and 35. The rings 34 and 35 are supported respectively, in turn, by a plurality of support rods 36 and a support screen 37.

A clear glass coil 38 is supported by a plurality of upright support rods 39 and surrounds the ultraviolet lamp 32. In this position, the segmented samples flowing through the glass coil 38 are irradiated by ultraviolet radiation, a fan 40 cools the unit 30.

The glass tube 33 is clear glass and serves as a filter to pass ultraviolet wavelengths of between about 290 millimicrons and about 400 millimicrons, and to block the shorter ultraviolet wavelength. The result is that all of the cyanide complexes including iron complexes are dissociated, except the strong cobalt complex is only partially dissociated. By using the alkaline samples, instead of acidified ones, for irradiation, even the cobalt complex breaks down.

In operation, samples are passed through the glass coil 38 to produce the irradiated samples in which cyanides have been dissociated, without dissociating thiocyanate.

Figure 3:
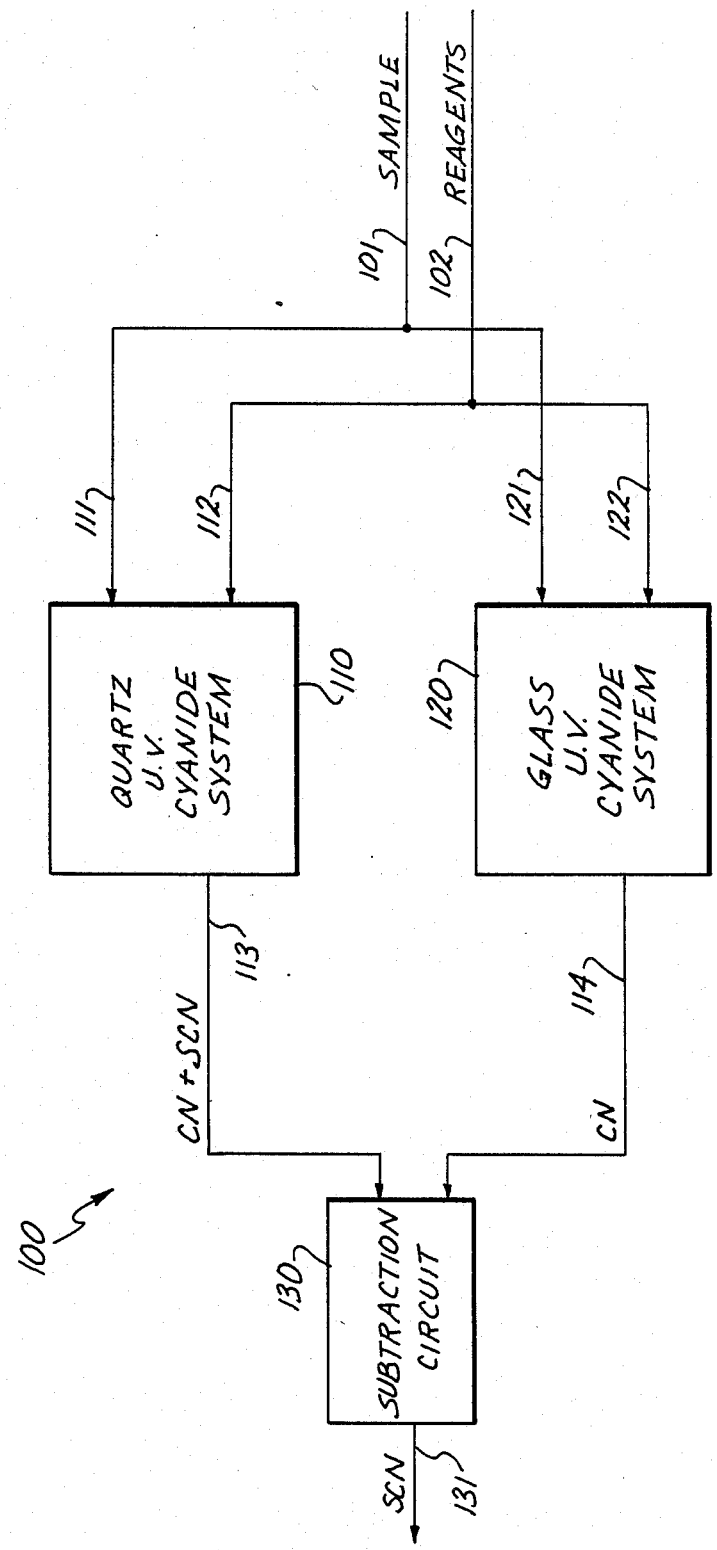
FIG. 3 is a block diagram of a two-channel system for detecting and measuring thiocyanate in samples, according to the present invention.

FIG. 3 is a block diagram of a two-channel system 100 for detecting thiocyanate in the samples. In one channel, the glass system 10 is employed to provide output signals indicative of the complete cyanides. The second channel includes a conventional quartz system 110, as disclosed in the foregoing mentioned publication, to provide an indication of the complete cyanides as well as thiocyanates from the same samples.

Samples are communicated through line 101, and reagents are communicated through line 102, and are coupled to inputs 111 and 112 of quartz UV cyanide system 110 and glass UV cyanide system 10. System 110 is similar to system 10, and employs a conventional quartz ultraviolet irradiation unit (not shown), in place of the filtered ultraviolet irradiation unit 30, to provide a full spectrum of ultraviolet radiation, thereby dissociating all of the cyanides and thiocyanates in each sample.

The output of system 110 is an electrical signal 113 indicative of all of the dissociated cyanide and thiocyanate for each sample. The output of system 10 is an electrical signal 114 indicative of the dissociated cyanides without any thiocyanate (SCN). These two output signals may be produced by the output of a colorimeter, such as a colorimeter 65 in FIG. 1. Other conventional techniques may also be employed for generating the signals. The signals are coupled to a suitable conventional subtraction circuit 130, which produces an electrical output signal 131 indicative of the difference between the input signals 113 and 114. Thus, the output signal 131 indicates the amount of thiocyanate (SCN), in the samples under test.

Thus, the method and apparatus of this invention provides convenient measurements of complete cyanides and also of thiocyanate contained in the samples, if desired.

The quartz system 110 differs from the system 10, only by the fact that the glass tube 33 is replaced with a quartz tube (not shown), and that the acid mixture is added with the nitrogen to the samples prior to irradiation. Thus, only minor differences exist between the two systems.

Therefore, the signal 131 is the difference between the two measurements made by the two channels, and provides an indication of the thiocyanate contained in each sample under test.

An advantage of the two-channel technique for measuring thiocyanate, is that color and turbidity of the samples, does not interfere with the measurements. Conventional direct colormetric measurements of thiocyanate are subjected to interferences from color and turbidity, when present in the samples. With the automated system of this invention, total cyanide, which completely includes all the strong cyanide complexes (even the strong cobalt complex), is conveniently measured without the presence of thiocyanate.

While a particular embodiment of the present invention has been disclosed, it is to be understood that various different modifications are possible and are contemplated within the true spirit and scope of the appended claims. For example, there are other techniques for filtering the ultraviolet irradiation, such as by eliminating the tube 33, and using only the glass coil 38 to serve as the filter. There is no intention, therefore, of limitations to the exact abstract or disclosure herein presented.

We claim:

1. In a system for measuring cyanide as well as thiocynates in a sample, the combination comprising:
    photo illumination means for producing the entire spectrum of ultraviolet radiation to dissociate cyanides contained in an alkaline sample;
    low pass ultraviolet filter means interposed between the photo illumination means and the sample to be tested, to prevent substantially the dissociation of thiocyanates in the sample, and for passing only lower frequency ultraviolet radiation of wavelengths between about 290 millimicrons and about 400 millimicrons to produce an irradiated sample in which substantially all other cyanides have been dissociated;
    thin-film distillation means for separating cyanide from the irradiated sample to produce recovered cyanide for measurement purposes;
    measuring means for receiving the recovered cyanide and for generating a recordable signal indicative of recovered cyanide quantity.

2. The combination recited in claim 1, wherein;
    the photoillumination means includes an ultraviolet light.

3. The combination recited in claim 1, wherein;
    the filter means includes a glass tube disposed around the photoillumiation means.

4. The combination recited in claim 1, wherein;
    the filter means includes a glass coil disposed around the photoillumination means through which a sample to be tested is passed.

5. The combination as recited in claim 1, further comprising:
    means for adding an acid to said irradiated sample between said filter means and said thin-film distillation means, to achieve total breakdown of cyanide complexes, without dissociating the thiocyanate.

6. The combination recited in claim 1, wherein said filter means includes a clear glass filter.

7. A method of measuring cyanides in a sample, comprising:
    using photoillumination components for producing ultraviolet radiation to dissociate cyanides contained in an alkaline sample;
    interposing a filter between the photoillumination means and an alkaline sample to be tested for passing lower frequency ultraviolet radiation to produce an irradiated sample in which cyanides have been dissociated, while blocking high frequency ultraviolet radiation to inhibit thiocyanate dissociation;
    separating cyanide from the irradiated sample to produce recovered cyanide for measurement purposes; and
    measuring the recovered cyanide to generate a recordable signal indicative of recovered cyanide quantity.

8. The method as recited in claim 7, further comprising the step of measuring thiocyanate in the sample by:
    using a quartz ultraviolet irradiation unit in conjunction with measuring components to generate a signal indicative of the amount of recovered cyanide and thiocyanate; and
    using a substraction circuit responsive to a first input signal representing said signal indicative of recovered cyanide quantity, said substraction circuit being also responsive to a second input signal representing said signal indicative of the amount of cyanide and thiocyanate, to generate a recordable output signal indicative of the difference between said first and second input signals.

9. The method as recited in claim 7, further comprising;
    acidifying the irradiated sample and subjecting the acidified sample to thin-film distillation.

10. The method as recited in claim 9, further comprising;
    absorbing HCN from the output of the thin-film distillation.

11. A method of measuring thiocyanate in a sample, comprising;
    using a quartz ultraviolet irradiation unit in conjunction with measuring components to generate a first signal indicative of the amount of recovered cyanide and thiocyanate:

using a glass irradiation unit in conjunction with measuring components to generate a second signal indicative of the amount of recovered cyanide; and using a subtraction circuit responsive to the first and second signals to generate a recordable signal indicative of the difference between the first and second signals.

* * * * *